United States Patent
Fitoussi et al.

[11] Patent Number: 5,984,373
[45] Date of Patent: Nov. 16, 1999

[54] LUER CONNECTOR

[75] Inventors: Gilles Fitoussi, Kibbutz Bar-Am; Elisha Amir, Moshav Livnim, both of Israel

[73] Assignee: Elcam Plastic Kibbutz Bar-Am, Kibbutz Bar-Am, Israel

[21] Appl. No.: 09/041,033

[22] Filed: Mar. 12, 1998

[51] Int. Cl.$^6$ ..................................................... F16L 15/00
[52] U.S. Cl. .......................... 285/92; 285/332; 285/334.4; 604/283
[58] Field of Search ................ 285/92, 332, 334.4, 285/423; 604/283

[56] References Cited

U.S. PATENT DOCUMENTS

| | | |
|---|---|---|
| 4,452,473 | 6/1984 | Ruschke ............................. 285/332 X |
| 5,047,021 | 9/1991 | Utterberg . | |
| 5,303,964 | 4/1994 | Yi ......................................... 285/92 X |
| 5,620,427 | 4/1997 | Werschmidt . | |
| 5,702,374 | 12/1997 | Johnson ............................... 285/332 X |

Primary Examiner—Dave W. Arola
Attorney, Agent, or Firm—Oliff & Berridge, PLC

[57] ABSTRACT

A luer-type connector comprising a male-component formed with a locking nozzle having a co-axially extending lumen, and a locking collar rotatable over the nozzle and having a rear end, and formed with an internal thread for screw coupling with a radially extending annular lug of a mating female-component of the luer-type connector. The nozzle is formed with ridge having a rear, radially extending abutting wall surface terminating at an acute edge. The locking collar is formed with a ridge-engaging portion consisting of a first wall surface rearwardly tapering, and a second wall surface radially extending and adapted for engagement with the abutting wall surface of the ridge, whereby the first wall surface is adapted for frictional displacement along the acute edge and the second wall surface prevents further forward axial displacement of the locking collar with respect to the nozzle.

7 Claims, 3 Drawing Sheets

LUER CONNECTOR

FIELD OF THE INVENTION

The present invention is generally in the field of luer-type connectors and in particular the invention is related to an improved male luer-type component fitted with a rotatable locking collar, the latter at times referred to as a "hub".

BACKGROUND OF THE INVENTION

In a variety of medical procedures it is required to provide fast connecting means for connecting fluid transferring tubes to one another, for connecting tubes to branching devices and to different medical devices, as well as to a variety of flow control valves, etc.

For these and many other purposes, a variety of luer-type connectors are commonly utilized, which connectors provide on the one hand fast connecting and disconnecting, and on the other hand, provide reasonable reliability and security which is a critical requirement of such connectors to prevent un-intentional disconnection between the components, which under certain circumstances may be fatal for the patient or for the medical staff which may be exposed to contaminated body fluids. Still another problem which may occur in a connector non-tightly coupled is entry of air into the system which may be fatal.

Luer-type connectors are thus commonly in use. Various designs of luer-type connectors are available in which a tapered nozzle of a male-component is dimensioned to snugly, frictionally fit into a tapered socket female-component of the fitting, with a collar member rotatably retained over the male component and adapted for screw coupling with an annular threaded flanged portion of the female-component.

A variety of luer-type connectors are available and special consideration has been given to increased connecting force which at times may be required, e.g. to facilitate high pressure fluid flow through the connecting and to prevent ingress of air into the system or, for extra precaution to prevent loss of high risk fluids such as contaminated body fluids. However, excessive rotational force applied to the collar may eventually lead to disengagement of the collar from the male-component, entailing decoupling of the connection which may result in a hazardous outcome.

In particular, the problem of disengagement of the collar from the male-component may occur while transferring fatty which have a lubricating effect on the coupling, or even in case of unintentional excessive force applied to the collar, e.g. in case of stress of the medical staff.

Several attempts have been made to prevent disengagement of the rotatable collar from the male component. U.S. Pat. No. 5,047,021 discloses in FIGS. 2a, 9 and 10 some prior art arrangements in which the male-component is formed at a rear end of its nozzle with a radial abutting shoulder adapted for arresting a corresponding abutting ridge of the collar, thus preventing further axial displacement of the collar over the nozzle once said abutting walls engage one another. The drawback of such an arrangement is that no frictional resistance exists between the rotatable collar and the nozzle member whereby essentially all the fastening force is directed to screw coupling between the collar and the female-component, which may result in mechanical fracture of the components.

U.S. Pat. No. 5,620,427 discloses in FIGS. 8a–8c an arrangement in which the male-component is formed at a rear end thereof with an inclined surface adapted for engaging a corresponding inclined surface of the collar, whereby excessive tightening of the collar is supposed to cause a hard stop and prevent disengagement of the collar from the male-component during engagement of said inclined surfaces. However, a serious drawback of this arrangement resides in that excessive force will eventually cause the inclined surface of the collar to slip over the inclined surface of the nozzle until disengagement of the collar from the male-component, leading to some undesirable results.

It is thus an object of the present invention to provide a luer-type connector in which the above-referred to disadvantages are significantly reduced or overcome.

A further object of the invention resides in providing an improved male-component of a luer-connector in which the collar is prevented from disengaging therefrom.

SUMMARY OF THE INVENTION

According to the present invention there is provided a luer-type connector comprising a male-component formed with a locking nozzle having a co-axially extending lumen, and a locking collar rotatable over said nozzle, said locking collar having a rear end and being formed with an internal thread for screw coupling with a radially extending annular lug of a mating female-component of the luer-type connector, the invention characterized in that the nozzle is formed with ridge having a rear, radially extending abutting wall surface said wall surface terminating at an acute edge; the locking collar is formed with a ridge-engaging portion consisting of a first wall surface rearwardly tapering, and a second wall surface radially extending and adapted for engagement with the abutting wall surface of the ridge, whereby the first wall surface is adapted for frictional displacement along the acute edge and the second wall surface prevents further forward axial displacement of the locking collar with respect to the nozzle.

By a preferred embodiment of the present invention, the first wall surface of the locking collar is inclined at an angle of between 5° to 12° with respect to a longitudinal axis thereof. A preferred inclination of the first wall surface is about 8°.

By another embodiment of the present invention, the ridge of the nozzle comprises a first portion tapering towards a front end thereof, and an intermediate portion extending between a rear end of said tapering portion and the radially extending abutting wall surface. Preferably, said intermediate portion is essentially cylindrical and co-axial with the nozzle's lumen.

By another aspect of the present invention, there is provided a male-component for use in conjunction with a mating female-component of a luer-type connector, said male-component having the features as characterized hereinabove.

BRIEF DESCRIPTION OF THE DRAWINGS

For better understanding, the invention will now be described, by way of example only, with reference to a non-limiting specific embodiment, in which.

DETAILED DESCRIPTION OF A SPECIFIC EMBODIMENT

Figure 1A:
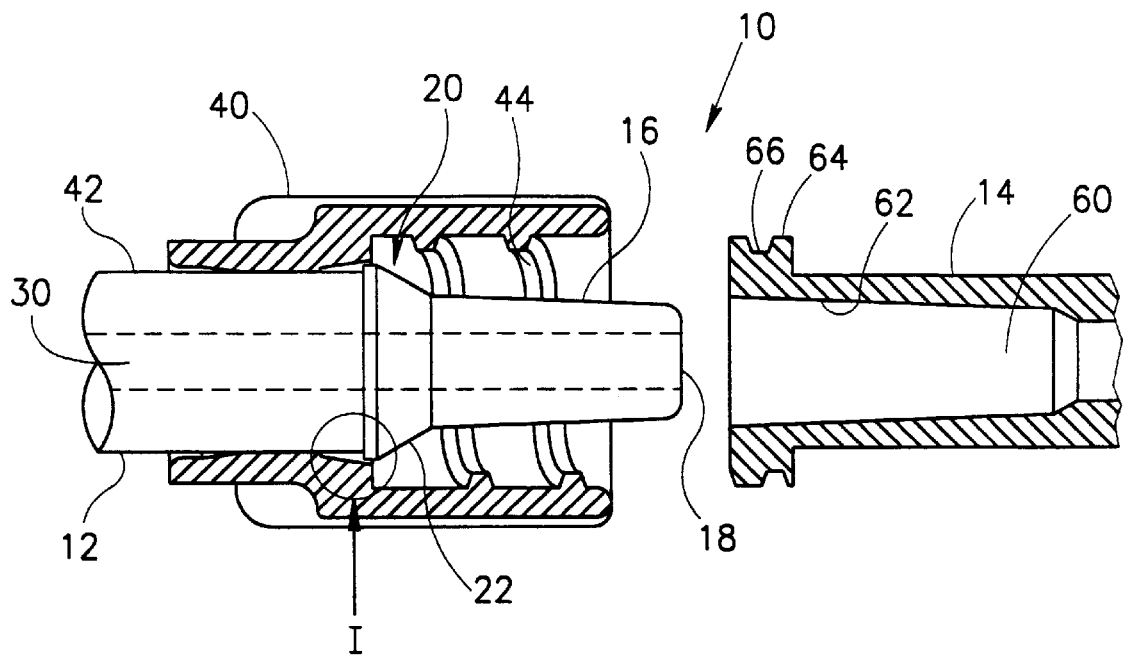
FIG. 1A is a longitudinal cross-sectional view of a luer-type connector in accordance with the present invention, with the male and female components disengaged from one another.

FIG. 1A illustrates a luer-type connector generally designated 10 consisting of a male-component 12 and a female-component 14. Male-component 12 comprises a nozzle portion 16 tapering towards its front end 18. At a rear end of nozzle 16 there is a ridge portion 20 consisting of a first portion 22 tapering forwardly and an intermediate portion 24 being essentially cylindrical and terminating at an essentially radial wall surface 26 constituting a right angle edge 28 therebetween.

Male-component 12 is further formed with a co-axial lumen 30.

Figure 1B:
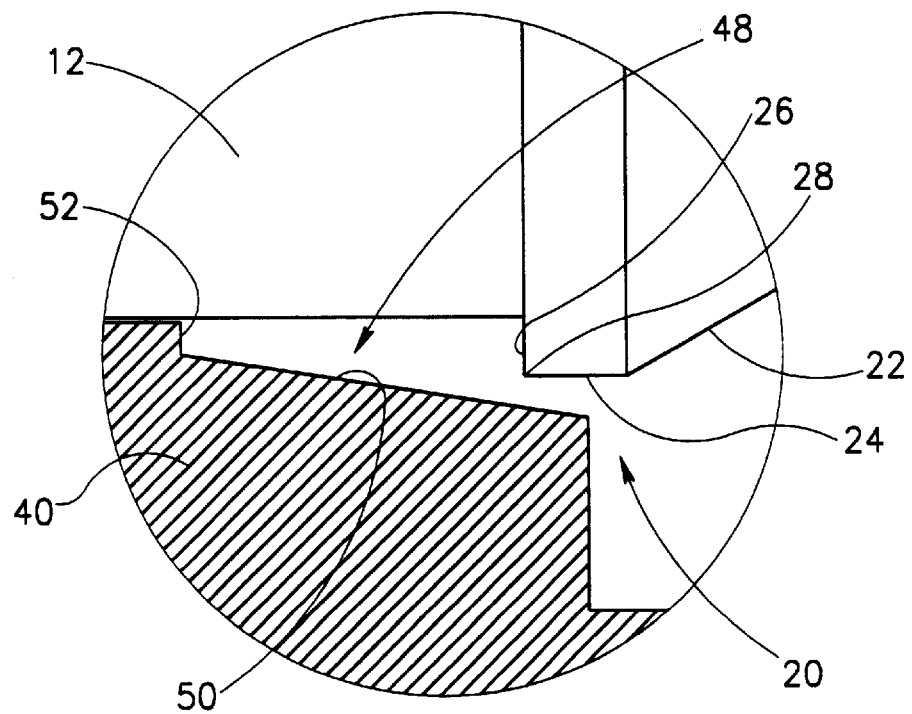
FIG. 1B is an enlargement of portion marked I in FIG. 1A.

A locking collar 40 is rotatably mounted over a cylindrical portion 42 at a rear end of the male-component 12. The locking collar 40 is formed with an internal threading 44 and as can best be seen in the enlarged view of FIG. 1B, has a ridge-engaging portion generally designated 48 consisting of a first wall surface 50 tapering towards a rear end of the locking collar, and a second wall surface 52 extending essentially radially.

Female-component 14 of the luer-type connector 10 has a lumen 60 with tapered walls 62 for frictional engagement over tapering nozzle 16 of the male component 12. Female component 14 has at its front end an annular lug 64 formed with a threading corresponding with that of the internal threading 44 of locking collar 40, as known per se.

In the position illustrated in FIG. 1A, the locking collar 40 is disposed in a rear-most position with respect to the male-component 12.

Figure 2A:
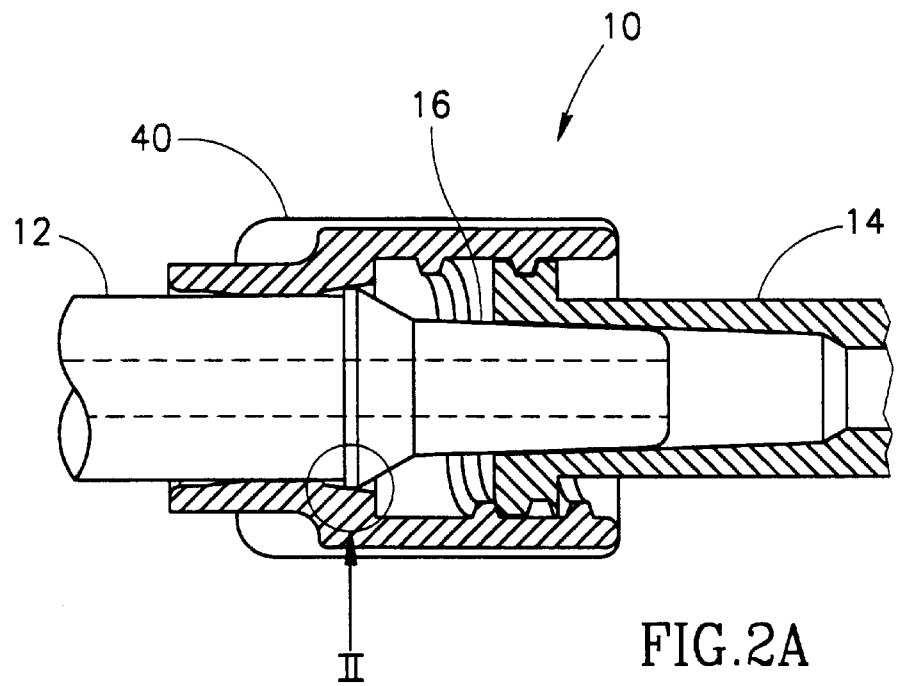
FIG. 2A is a longitudinal cross-section of the connector in accordance with the present invention with the male and female components in a connected but not secured position.
Figure 2B:
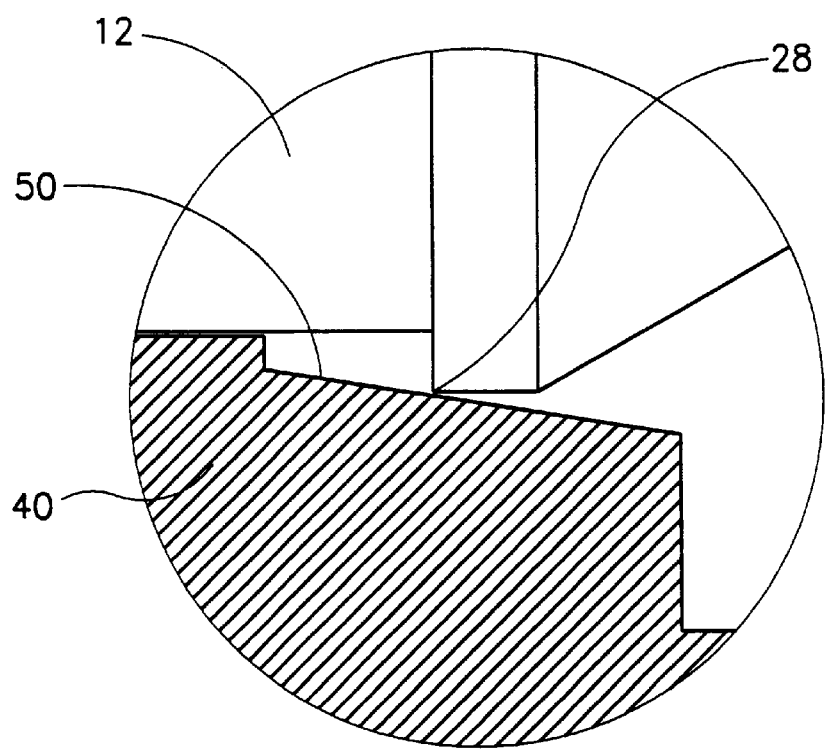
FIG. 2B is an enlargement of portion II seen in FIG. 2A.

Further attention is now directed to FIGS. 2A and 2B illustrating the position of luer-type connector 10 according to the invention, in which the female-component 14 is frictionally engaged over the nozzle 16 of the male-component 12. The male and female components are also partially locked with the locking collar 40 screw coupled with threading 66 of lug 64 of the female-component 14.

As noticeable, in particular in FIG. 2B, upon further tightening the screw coupling of the locking collar 40 with the threaded lug 64 of female-component 14, edge 28 of the male-component frictionally engages with the first wall portion 50 of the locking collar 40, wherein a more significant force is required for further tightening the screw coupling with the female-component 14.

Figure 3A:
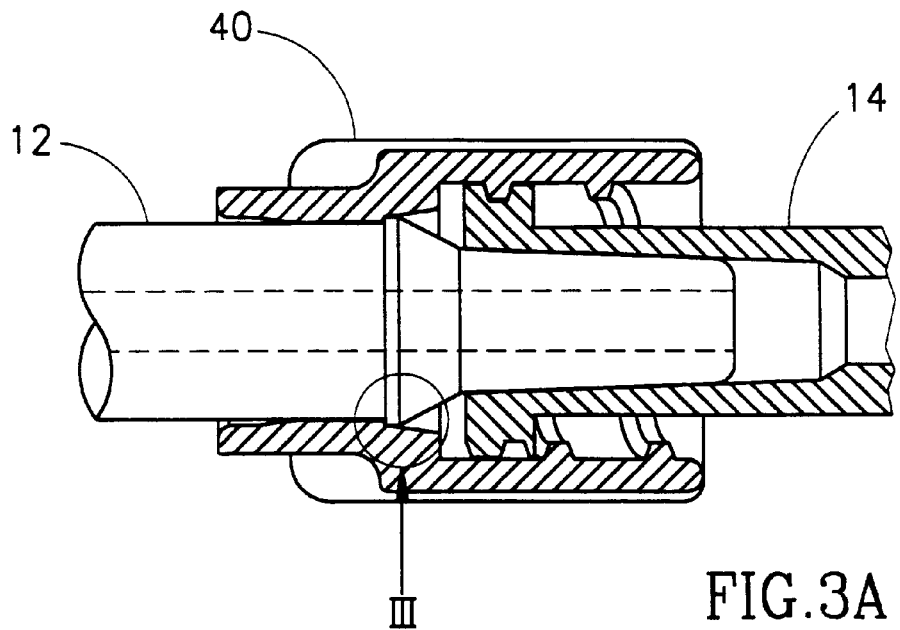
FIG. 3A is a longitudinal cross-section of the connector of the present invention in which the male and female components are engaged in a secured position.
Figure 3B:
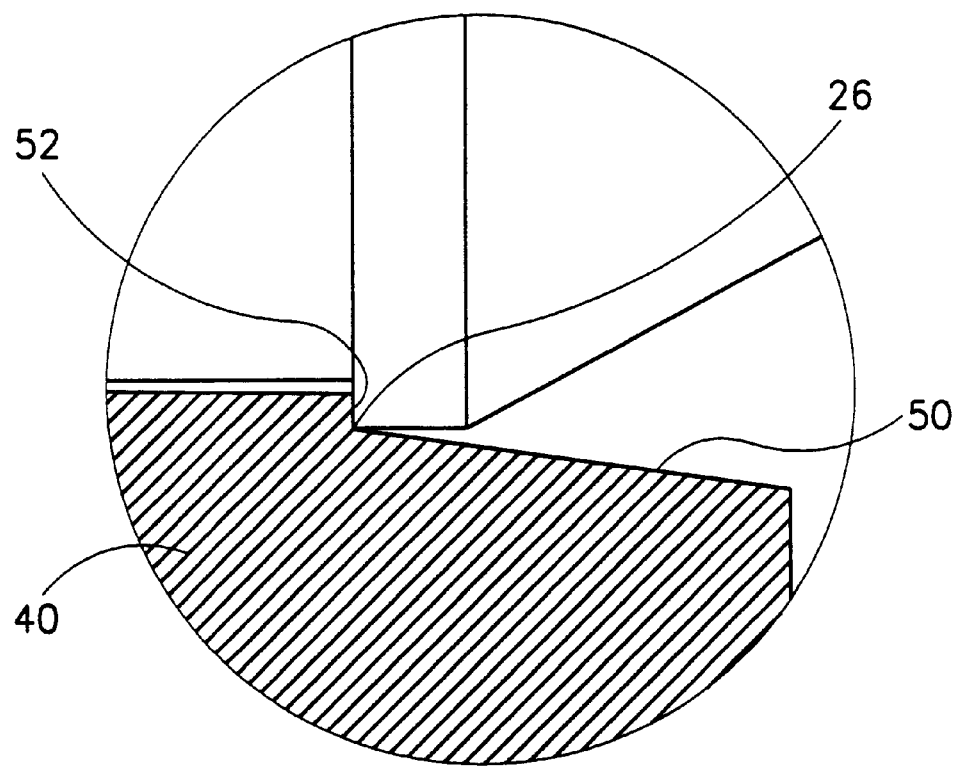
FIG. 3B is an enlargement of portion III seen in FIG. 3A.

FIGS. 3A and 3B illustrate the situation after significant force has been applied to the locking collar 40 for screw engagement with the female-component 14, resulting in displacement of the locking collar 40 to a most forward position, in which the second wall portion 52 of the locking collar 40 engages the abutting, radial wall portion 26 of the male-component 12 thus preventing further displacement of the locking collar 40 in a forward direction, whereby it is ensured that the locking collar will not disengage from the male component 12 and that the connector 10 remains securely locked.

Experimentally it was found out that best results were obtained when the first wall surface 50 of the locking collar 40 is inclined at an angle of about between 5° to 12° with respect to the longitudinal axis of the connector. However, a preferred inclination was found to be about 8°.

It will be readily understood that the above may be carried out in other ways, e.g. having intermediate portion 24 of the ridge portion 20 tapering forward rather than being cylindrical, as long as edge 28 remains acute.

We claim:

1. A luer-type connector comprising a male-component formed with a locking nozzle having a co-axially extending lumen, and a locking collar rotatable over said nozzle, said locking collar having a rear end and being formed with an internal thread for screw coupling with a radially extending annular lug of a mating female-component of the luer-type connector, the nozzle being formed with a ridge, the ridge having a radially extending abutting wall surface facing the rear end of the locking collar, and an outer peripheral surface connected to the abutting wall surface at an edge, an angle between the outer peripheral surface of the ridge and the abutting wall surface of the ridge no greater than 90°, the locking collar being formed with a ridge-engaging portion comprising a first wall surface that tapers toward the rear end of the locking collar and that forms an angle of greater than 0° with respect to the outer peripheral surface of the ridge, and a second wall surface radially extending and engageable with the abutting wall surface of the ridge, the first wall surface engaging the edge of the ridge and being frictionally displaceable along the edge of the ridge and the second wall surface preventing further forward axial displacement of the locking collar with respect to the nozzle.

2. A luer-connector according to claim 1, wherein the first wall surface of the locking collar tapers at an angle of about between 5°–12° with respect to a longitudinal axis thereof.

3. A luer-connector according to claim 1, wherein the ridge of the nozzle comprises a first portion tapering towards a front end thereof, and said outer peripheral surfaces include and an intermediate portion extending between a rear end of said tapering portion and the radially extending abutting wall surface.

4. A luer-connector according to claim 3, wherein said intermediate portion is essentially cylindrical and co-axial with the nozzle.

5. A luer-type connector according to claim 1, wherein the angle between the outer peripheral surface of the ridge and the first wall surface of the locking collar is in a range of from about 5° to about 12°.

6. A luer-type connector according to claim 1, wherein the angle between the outer peripheral surface of the ridge and the first wall surface of the locking collar is about 8°.

7. A luer-type connector comprising a male-component formed with a locking nozzle having a co-axially extending lumen, and a locking collar rotatable over said nozzle, said locking collar having a rear end and being formed with an internal thread for screw coupling with a radially extending annular lug of a mating female-component of the luer-type connector, the nozzle being formed with a ridge, the ridge having a radially extending abutting wall surface facing the rear end of the locking collar, and an outer peripheral surface connected to the abutting wall surface at an edge, the locking collar being formed with a ridge-engaging portion comprising a first wall surface that tapers toward the rear end of the locking collar and that forms an angle of greater than 0° with respect to the outer peripheral surface of the ridge, and a second circumferentially continuous wall surface radially extending and engageable with the abutting wall surface of the ridge, the first wall surface engaging the edge of the ridge being frictionally displaceable along the edge of the ridge and the second wall surface preventing further axial displacement of the locking collar with respect to the nozzle.

* * * * *